(12) United States Patent
Huizenga et al.

(10) Patent No.: US 11,203,561 B2
(45) Date of Patent: Dec. 21, 2021

(54) STABILIZATION OF POLYHYDRIC ALCOHOLS BY STEAM INJECTION

(71) Applicant: SHELL OIL COMPANY, Houston, TX (US)

(72) Inventors: Pieter Huizenga, Amsterdam (NL); Kai Jürgen Fischer, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 6 days.

(21) Appl. No.: 16/970,449

(22) PCT Filed: Feb. 19, 2019

(86) PCT No.: PCT/EP2019/054066
§ 371 (c)(1),
(2) Date: Aug. 17, 2020

(87) PCT Pub. No.: WO2019/162260
PCT Pub. Date: Aug. 29, 2019

(65) Prior Publication Data
US 2020/0377438 A1  Dec. 3, 2020

Related U.S. Application Data

(60) Provisional application No. 62/633,154, filed on Feb. 21, 2018.

(51) Int. Cl.
| | |
|---|---|
| *C07C 29/84* | (2006.01) |
| *B01D 3/00* | (2006.01) |
| *B01D 3/40* | (2006.01) |
| *B01D 3/42* | (2006.01) |
| *C07C 31/20* | (2006.01) |
| *C07C 31/22* | (2006.01) |

(52) U.S. Cl.
CPC .............. *C07C 29/84* (2013.01); *B01D 3/40* (2013.01); *B01D 3/42* (2013.01); *C07C 31/202* (2013.01); *C07C 31/205* (2013.01); *C07C 31/207* (2013.01); *C07C 31/225* (2013.01)

(58) Field of Classification Search
CPC .................................. C07C 29/84; B01D 3/40
See application file for complete search history.

(56) References Cited

U.S. PATENT DOCUMENTS

| | | | |
|---|---|---|---|
| 2,960,447 A | 11/1960 | Anderson et al. | |
| 2,993,840 A | 7/1961 | Poincet | |
| 4,935,102 A | 6/1990 | Berg | |
| 4,966,658 A | 10/1990 | Berg | |
| 5,423,955 A | 6/1995 | Berg | |
| 2011/0312050 A1 | 12/2011 | Zhang et al. | |
| 2013/0284584 A1 | 10/2013 | Xiao et al. | |

FOREIGN PATENT DOCUMENTS

| | | |
|---|---|---|
| CN | 1634823 A | 7/2005 |
| CN | 102643165 A | 8/2012 |
| EP | 3126315 A1 | 2/2017 |
| WO | 2014193889 A1 | 12/2014 |
| WO | 2016091751 A1 | 6/2016 |

OTHER PUBLICATIONS

International Search Report and Written Opinion received for PCT Patent Application No. PCT/EP2015/078680, dated Jan. 25, 2016, 2019, 9 pages.
Rogalski et al., "Ebulliometers modified for the Accurate Determination of Vapour-liquid Equilibrium", Fluid Phase Equilibria, vol. 5, Issue No. 1-2, 1980, pp. 97-112.
Yufeng, "Separation of Glycol and 1, 2-propanediol by Heterogeneous Azeotropic Distillation", Contemporary Chemical Industry, vol. 40, Issue No. 6, Jun. 30, 2011, pp. 560-562. (Copy of English abstract only).
International Search Report and Written Opinion received for PCT Patent Application No. PCT/EP2019/054066, dated May 16, 2019, 9 pages.

*Primary Examiner* — Sikarl A Witherspoon
(74) *Attorney, Agent, or Firm* — Shell Oil Company

(57) ABSTRACT

A method for separating monoethylene glycol (MEG) from one or more oxygenates. The method includes providing a stream comprising MEG and one or more oxygenates to a distillation column, providing a water feed stream to a bottom of the distillation column, and removing a recovery stream comprising MEG from the distillation column. The distillation column is operated at higher temperatures than the thermal stability of MEG and the one or more oxygenates.

18 Claims, 1 Drawing Sheet

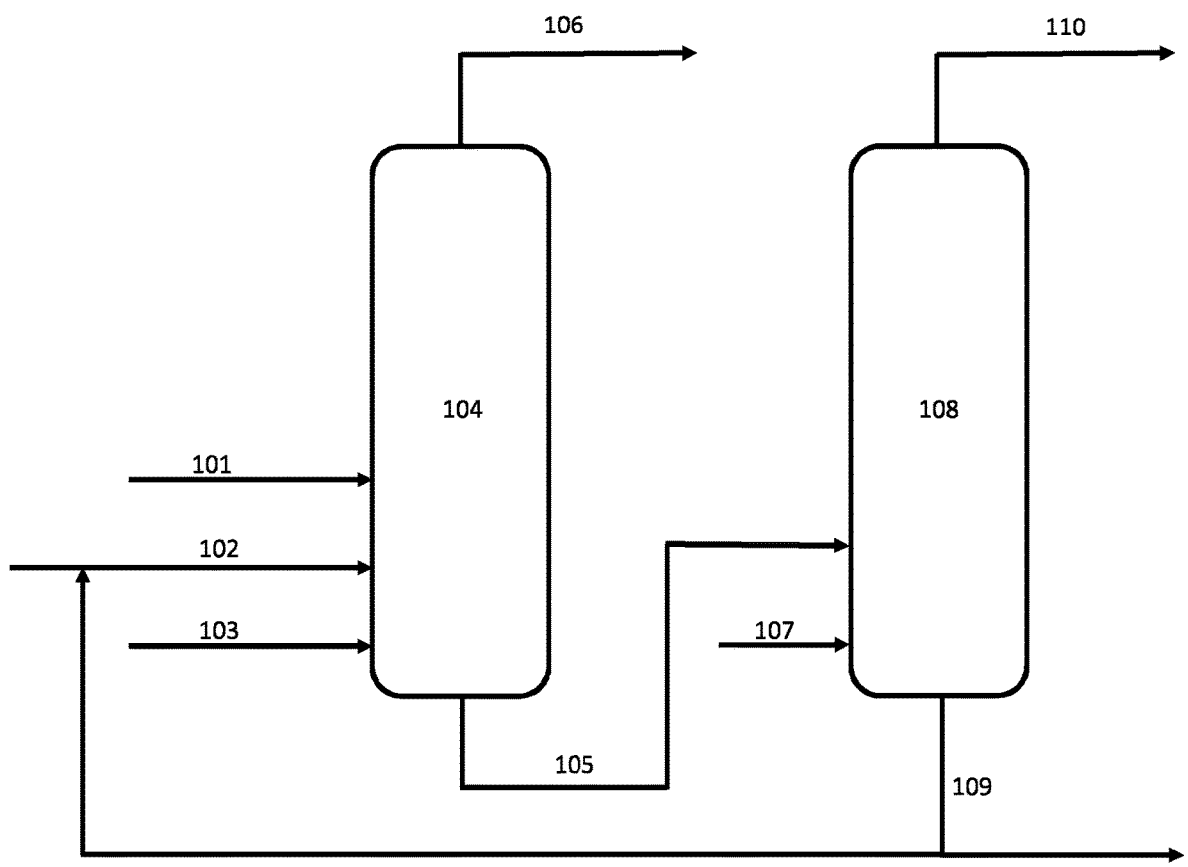

STABILIZATION OF POLYHYDRIC ALCOHOLS BY STEAM INJECTION

CROSS REFERENCE TO RELATED APPLICATIONS

This is a national stage application of International Application No. PCT/EP2019/054066, filed 19 Feb. 2019, which claims benefit of priority to U.S. Provisional Application No. 62/633,154, filed 21 Feb. 2018.

FIELD OF THE INVENTION

The present disclosure relates to a process for the selective separation of glycols. More particularly, in certain embodiments, the present disclosure relates to a process for the selective separation of glycols utilizing water injection to prevent the formation of condensation reaction by-products.

BACKGROUND OF THE INVENTION

Ethylene glycol and propylene glycol are valuable materials with a multitude of commercial applications, e.g. as heat transfer media, antifreeze, and precursors to polymers, such as PET. Ethylene and propylene glycols are typically made on an industrial scale by hydrolysis of corresponding alkylene oxides, which are the oxidation products of ethylene and propylene, produced from fossil fuels.

In recent years, increased efforts have focused on producing chemicals, including glycols, from renewable feedstocks, such as sugar-based materials. For example, US 2011/0312050 describes a continuous process for the catalytic generation of polyols from cellulose, in which the cellulose is contacted with hydrogen, water and a catalyst to generate an effluent stream comprising at least one polyol. The entirety of US 2011/0312050 is hereby incorporated by reference.

As with many chemical processes, the reaction product stream in these reactions comprises a number of desired materials, diluents, by-products and other undesirable materials. In order to provide a high value process, the desirable product or products must be obtainable from the reaction product stream in high purity with a high percentage recovery of each product and with as low as possible use of energy and complex equipment. In known processes to make glycols, the glycols are usually present at high dilution in a solvent, typically water. The water is usually removed from the glycols by distillation. From biomass based processes, the main glycol constituents in the reaction product stream are monoethylene glycol (MEG), monopropylene glycol (MPG) and 1,2-butanediol (1,2-BDO). 1,2-pentanediol (1,2-PDO) and 1,2-hexanediol (1,2-HDO) may also be present. Subsequent purification of the glycols may then be carried out by fractional distillation. The known processes can have high costs both in terms of capital and operational expenditure.

The separation of these glycols by fractional distillation is complicated due to the similarity in boiling points, particularly between MEG and 1,2-BDO (respectively 198 and 196.8° C.). Further, the isolation of a pure MEG overheads stream by fractional distillation from a mixture comprising MEG and 1,2-BDO is made impossible by the formation of a homogeneous minimum boiling azeotrope between MEG and 1,2-BDO at atmospheric pressure.

Recently, it had been discovered that MEG can be effectively separated with high recovery and excellent MEG product purity from a mixture comprising MEG and 1,2-BDO by distilling said mixture in a distillation column wherein a feed of glycerol is provided to the top of the column. The presence of glycerol in the distillation column changes the relative volatilities of MEG and 1,2-BDO and breaks the azeotrope that exists between the two. WO 2016/091751, the entirety of which is hereby incorporated by reference, describes such a process.

In that process, the glycerol may then be separable from the MEG in a recovery column. However, the repeated heating in the recovery step may lead to decomposition of the desired glycol products, as well as decomposition of glycerol. Briefly, condensation reactions may occur which destabilize any alcohols, glycols, triols, and polyhydric alcohols, allowing them to thermally degrade through water releasing condensation reactions. For example, acrolein may be formed from the decomposition of glycerol and 1,4-dioxane may be formed from the decomposition of diethylene glycol.

One current method to mitigate this problem is to limit the bottom temperature of the recovery column to 180° C. and to also restrict the exposure time the feeds are subjected to high temperatures. However, operating the recovery column at reduced temperatures and with reduced exposure times limits the glycol recovery in the glycerol extractive distillation solvent regeneration column.

It is desirable to develop an improved method of extractive distillation and recovery of MEG that does not produce unwanted thermal decomposition products.

SUMMARY OF THE INVENTION

The present disclosure relates to a process for the selective separation of glycols. More particularly, in certain embodiments, the present disclosure relates to a process for the selective separation of glycols utilizing water injection to prevent the formation of condensation reaction by-products.

In one embodiment, the present disclosure describes a method comprising: providing a mixture feed stream comprising MEG and glycerol to a solvent recovery column; providing a water feed stream to a bottom of the solvent recovery column; operating the solvent recovery column; and removing an MEG recovery stream from the solvent recovery column.

In another embodiment, the present disclosure describes a method comprising: providing a reaction product stream to an extractive distillation column; providing a glycerol feed stream to the extractive distillation column above the reaction product stream; providing a water feed stream to a bottom of the extractive distillation column; operating the extractive distillation column; and removing a mixture feed stream comprising MEG and glycerol from the extractive distillation column.

In another embodiment, the present disclosure describes a method comprising: providing a reaction product stream to an extractive distillation column; providing a glycerol feed stream to the extractive distillation column above the reaction product stream; providing a first water feed stream to a bottom of the extractive distillation column; operating the extractive distillation column; removing a mixture feed stream comprising MEG and glycerol from the extractive distillation column; providing the mixture feed stream to a solvent recovery column; providing a second water feed stream to a bottom of the solvent recovery column; operating the solvent recovery column; and removing an MEG stream from the solvent recovery column.

The features and advantages of the present disclosure will be readily apparent to those skilled in the art. While numerous changes may be made by those skilled in the art, such changes are within the spirit of the disclosure.

BRIEF DESCRIPTION OF THE DRAWINGS

A more complete and through understanding of the present embodiments and advantages thereof may be acquired by referring to the following description taken in conjunction with the accompanied drawings.

FIG. 1 illustrates a schematic diagram of an exemplary, but non-limiting, embodiment of a process for the separation of glycols as described herein.

The features and advantages of the present disclosure will be readily apparent to those skilled in the art. While numerous changes may be made by those skilled in the art, such changes are within the spirit of the disclosure.

DETAILED DESCRIPTION OF THE INVENTION

The present disclosure relates to a process for the selective separation of glycols. More particularly, in certain embodiments, the present disclosure relates to a process for the selective separation of glycols utilizing water injection to prevent the formation of condensation reaction by-products.

Methods have been identified that allow for the separation of components with one or more alcohol (OH) functional groups at higher temperatures than the thermal stability of those components typically allow.

It has been discovered that adding a volatile component to a bottom of a distillation column, at a rate exceeding its solubility in the liquids, provides a partial pressure in the distillation column that limits unwanted thermal condensation reactions or elimination reactions that lead to the formation of the particular volatile component. More specifically, it has been discovered that the injection of steam into the bottom of hot process compartments, for example distillation bottoms, prevents the thermal degradation of molecules comprising OH groups.

The present disclosure describes a method of preventing condensation and water elimination reactions in distillation columns by injecting a stream of water into the bottom of the distillation column. In certain embodiments, the method described herein may be utilized to prevent the formation of ethylene oxide, diethylene glycol, triethylene glycol, tetraethylene glycol, polyethylene glycols, 1,4-dioxane (inter- and subsequent intramolecular), acetaldehyde, hydroxyacetone, 3-hydroxypropanal, acrolein, polyglycerols, formaldehyde, and various glycerol condensation dehydration products that occur in the distillation of mixtures containing MEG and glycerol.

In certain embodiments, the methods described herein may be utilized to prevent the formation of ethylene oxide, diethylene glycol, triethylene glycol, tetraethylene glycol, polyethylene glycols, 1,4-dioxane (inter- and subsequent intramolecular), acetaldehyde, hydroxyacetone, 3-hydroxypropanal, acrolein and formaldehyde that occur under the thermal conditions during distillation of mixtures containing MEG, glycols, alcohols, polyhydric alcohols, glycerol and sugar alcohols. It is to be understood, however, that the methods described herein may be applicable to other processes that involve thermal condensation and elimination reactions, such as decarboxylation of organic carbonates.

Without wishing to be limited to theory, it is believed that the steam injected into the bottom of the distillation columns used for both extractive distillation and solvent regeneration may protect both the solvent (for example glycerol) and the glycol components from degradation. It is believed that the steam continuously provides a water partial pressure that does not remain in the boiling liquid when not continuously fed to the bottom of the columns because of limited solubility at high temperature and low pressure. Such water partial pressure reduces and limits the driving force for the thermal condensation reactions when stripping the water vapor through the liquid. This allows for the distillation columns to be operated at higher pressures and temperatures than they can conventionally operate at allowing for a higher solvent capacity with smaller recycle streams and increased vapor density which leads to reduction of required column diameters. Furthermore, the MEG recovery from the solvent recovery column can be increased. The wider operating temperature window also provides opportunities for heat integration in integrated processes, because condensers can recover the heat spent in the reboilers, where the temperature of the cooling medium depends on the column pressure which is limited by the maximum boiling temperature following the thermal degradation constraints. Having a higher condensation temperature means to recover the heat at a higher and therefore more valuable temperature level.

In certain embodiments, the present disclosure describes a method comprising: providing a stream to a distillation column; providing a water feed stream to a bottom of the distillation column; operating the distillation column; and removing a recovery stream from the distillation column.

In certain embodiments, the stream may comprise one or more compounds having hydroxyl groups in their chemical structure. In certain embodiments, the stream may comprise a mixture of organic oxygenate components. In certain embodiments, the stream may comprise one or more glycols. In certain embodiments, the stream may comprise one or more diols. In certain embodiments, the stream may comprise one or more polyhydric alcohols.

In certain embodiments, the stream may comprise a mixture of one or more of the following compounds: MEG, MPG, 1,2-BDO, 1,2-PDO, and 1,2-HDO.

In certain embodiments, the stream may comprise a mixture feed stream comprising MEG and glycerol. In certain embodiments, the stream may comprise a mixture feed stream comprising MEG and sorbitol and/or erythritol. In certain embodiments, the distillation column may comprise a solvent recovery column or an extractive distillation column. In certain embodiments, the recovery stream may comprise an MEG recovery stream.

In certain embodiments, the water feed stream may be provided to the bottom of the distillation column by providing the water feed stream to a reboiler. In certain embodiments, the water feed stream may be provided to the bottom of the distillation column by combining the water feed stream with the stream. In certain embodiments, the water feed stream may be directly provided to the bottom of the distillation column.

In certain embodiments, the present disclosure describes a method comprising: providing a mixture feed stream comprising MEG and glycerol to a solvent recovery column; providing a water feed stream to a bottom of the solvent recovery column; operating the solvent recovery column; and removing an MEG recovery stream from the solvent recovery column.

In certain embodiments, the amount of MEG in the mixture feed stream may be an amount in the range of from 10 wt. % to 90 wt. % based on the overall weight of the mixture feed stream. In certain embodiments, the amount of MEG in the mixture feed stream may be an amount in the range of from 20 wt. % to 80 wt. % based on the overall weight of the mixture feed stream. In certain embodiments, the amount of MEG in the mixture feed stream may be an amount in the range of from 30 wt. % to 60 wt. % based on the overall weight of the mixture feed stream.

In certain embodiments, the amount of glycerol in the mixture feed stream may be an amount in the range of from 10 wt. % to 90 wt. % based on the overall weight of the mixture feed stream. In certain embodiments, the amount of glycerol in the mixture feed stream may be an amount in the range of from 20 wt. % to 80 wt. % based on the overall weight of the mixture feed stream. In certain embodiments, the amount of glycerol in the mixture feed stream may be an amount in the range of from 40 wt. % to 70 wt. % based on the overall weight of the mixture feed stream.

In certain embodiments, the mixture feed stream may further comprise one or more contaminants originating from upstream processes.

In certain embodiments, the water feed stream may be pure water or may comprise one or more contaminants that are more volatile than MEG. In certain embodiments, the water feed stream may comprise liquid water. In other embodiments, the water feed stream may comprise water vapor or steam.

In certain embodiments, the weight ratio of the amount of water feed stream provided to the solvent recovery column to the amount of mixture feed stream provided to the solvent recovery may be a ratio in the range of from 1:10,000 to 1:10. In certain embodiments, the weight ratio of the amount of water feed stream provided to the solvent recovery column to the amount of mixture feed stream provided to the solvent recovery may be a ratio in the range of from 1:1000 to 1:20. In certain embodiments, the weight ratio of the amount of water feed stream provided to the solvent recovery column to the amount of mixture feed stream provided to the solvent recovery may be a ratio in the range of from 1:500 to 1:50. In certain embodiments, the weight ratio of the amount of water feed stream provided to the solvent recovery column to the amount of mixture feed stream provided to the solvent recovery may be a ratio in the range of from 1:100 to 1:10. In certain embodiments, the weight ratio of the amount of water feed stream provided to the solvent recovery column to the amount of mixture feed stream provided to the solvent recovery may be a ratio in the range of from 1:10,000 to 1:100.

In certain embodiments, the water feed stream may be provided to the bottom of the solvent recovery column by providing the water feed stream to a reboiler. In certain embodiments, the water feed stream may be provided to the bottom of the solvent recovery column by combining the water feed stream with the mixture feed stream. In certain embodiments, the water feed stream may be directly provided to the bottom of the solvent recovery column.

In certain embodiments, operating the solvent recovery column may comprise operating the solvent recovery column at a temperature in the range of from 50° C. to 250° C. and a pressure in the range of from 0.1 to 400 kPa. In certain embodiments, operating the solvent recovery column may comprise operating the solvent recovery column at a temperature in the range of from 150° C. to 250° C. and a pressure in the range of from 0.1 to 100 kPa.

In certain embodiments, operating the solvent recovery column may comprise allowing the water from the water feed stream to vaporize in the solvent recovery column. In certain embodiments, operating the solvent recovery column may comprise allowing any vaporized water in the solvent recovery column to generate a water partial pressure in a vapor flow in the solvent recovery column. In certain embodiments, operating the solvent recovery column may comprise allowing any water vapor provided to the solvent recovery column to generate a water partial pressure in a vapor flow in the solvent recovery column. In certain embodiments, operating the solvent recovery column comprises allowing the water partial pressure to provide a thermodynamic driving force to avoid and/or limit thermal condensation and elimination reactions in the solvent recovery column.

In certain embodiments, operating the solvent recovery column may comprise generating a tops recovery stream and a bottoms recovery stream. In certain embodiments, a portion of the tops recovery stream may be recycled to the top of the solvent recovery column. In certain embodiments, a portion of the bottoms recovery stream may be recycled to the bottom of the solvent recovery column.

In certain embodiments, the tops recovery stream may comprise the MEG recovery stream. In certain embodiments, the tops recovery stream may be split into the MEG recovery stream and a water vapor stream with a partial condenser at the top of the solvent recovery column.

In certain embodiments, the tops recovery stream may comprise MEG and water with a water concentration depending on the configurations and conditions of the top section of the solvent recovery column. In cases where a partial condenser is used, the condensation temperature at given pressure level results in an equilibrium water content in the MEG recovery stream and an equilibrium MEG content in the water vapor stream. In certain embodiments, the partial condenser can be replaced with a rectification section in the top of the solvent recovery column. In such embodiments, the MEG recovery stream may be drawn as a side stream from an upper part of the solvent recovery column and the water vapor stream may be drawn as tops stream from the solvent recovery column.

In certain embodiments, the bottoms recovery stream may comprise glycerol and MEG with an MEG concentration in the range of from 0 wt. % to 5 wt. %. The temperature of the bottoms recovery stream may be in the range of from 100° C. to 250° C. In certain embodiments, a heat exchanger may be used to cool the bottoms recovery stream.

In certain embodiments, the bottoms recovery stream may be used as a glycerol feed stream to an extractive distillation column. In certain embodiments, portion ranging from 0 wt. % to 10 wt. % of the bottoms recovery stream may be withdrawn before the bottoms recovery stream is used as a glycerol feed stream to an extractive distillation column.

In certain embodiments, the mixture feed stream may be an extracted stream from an extractive distillation unit. In certain embodiments, the mixture feed stream may be an extracted stream from an extractive distillation unit used to extract MEG from 1,2-BDO. In certain embodiments, the extractive distillation unit may be a unit utilized to distill a reaction product stream generated from the hydrogenolysis of a saccharide containing feedstock.

In certain embodiments, the water feed stream may be recycled from the water vapor stream.

In certain embodiments, the present disclosure describes a method comprising: providing a reaction product stream to an extractive distillation column; providing a glycerol feed stream to the extractive distillation column above the reaction product stream; providing a water feed stream to a bottom of the extractive distillation column; operating the extractive distillation column; and removing a mixture feed stream comprising MEG and glycerol from the extractive distillation column.

In certain embodiments, the reaction product stream may comprise a reaction product stream generated from the hydrogenolysis of a saccharide containing feedstock. In certain embodiments, the reaction product stream may comprise MEG, MPG, and 1,2-BDO, and a solvent.

In certain embodiments, the amount of MEG present in the reaction product stream may be an amount in the range of from 0.1 wt. % to 30 wt. % of the reaction product stream. In certain embodiments, the amount MEG present in the reaction product stream may be an amount in the range of from 10 wt. % to 95 wt. % of the non-solvent fraction of the reaction product stream. In certain embodiments, the amount MEG present in the reaction product stream may be an amount in the range of from 30 wt. % to 80 wt. % of the non-solvent fraction of the reaction product stream.

In certain embodiments, the amount of MPG present in the reaction product stream may be an amount in the range of from 0.1 wt. % to 30 wt. % of the reaction product stream. In certain embodiments, the amount MPG present in the reaction product stream may be an amount in the range of from 2 wt. % to 45 wt. % of the non-solvent fraction of the reaction product stream. In certain embodiments, the amount MPG present in the reaction product stream may be an amount in the range of from 4 wt. % to 20 wt. % of the non-solvent fraction of the reaction product stream.

In certain embodiments, the amount of 1,2-BDO present in the reaction product stream may be an amount in the range of from 0.1 wt. % to 30 wt. % of the reaction product stream. In certain embodiments, the amount 1,2-BDO present in the reaction product stream may be an amount in the range of from 1 wt. % to 20 wt. % of the non-solvent fraction of the reaction product stream. In certain embodiments, the amount 1,2-BDO present in the reaction product stream may be an amount in the range of from 4 wt. % to 8 wt. % of the non-solvent fraction of the reaction product stream.

In certain embodiments, the solvent may comprise water. In certain embodiments, the amount of solvent present in the reaction product stream may be an amount in the range of from 10 wt. % to 90 wt. % of the reaction product stream.

In certain embodiments, the reaction product stream may comprise MEG and 1,2-BDO at a weight ratio of at least 5:1. In certain embodiments, the reaction product stream may comprise MEG and 1,2-BDO at a weight ratio of at least 25:1.

In certain embodiments, the reaction product stream may further comprise oxygenates, hydrocarbons, catalyst, degradation products, and gases. In certain embodiments, the reaction product stream may be introduced into the extractive distillation column. In certain embodiments, one or more treatment, separation and/or purification steps may be applied to the reaction product stream before it is introduced into the extractive distillation column. In certain embodiments, the reaction product stream is introduced into the extractive distillation column at the temperature level between ambient temperature and the column temperature at a reaction product stream feed location in the extractive distillation column.

In certain embodiments, the glycerol feed stream may be introduced into the extractive distillation column at the temperature level between ambient temperature and the column temperature at a glycerol feed stream feed location in the extractive distillation column. In certain embodiments, the glycerol feed stream may be introduced into the extractive distillation column above the point at which the reaction product stream is introduced into the extractive distillation column. In certain embodiments, the glycerol feed stream may comprise glycerol. In other embodiments, the glycerol feed stream may comprise glycerol and glycerol-like heavies, such as other polyhydric alcohols. In certain embodiments, the glycerol feed stream may be totally or partially replaced with a sorbitol and/or erythritol feed stream.

In certain embodiments, the glycerol feed stream may be introduced into the extraction distillation column at a rate such that the weight ratio of the glycerol feed stream to the reaction product stream introduced into the extractive distillation column is at least 1:20. In certain embodiments, the glycerol feed stream may be introduced into the extraction distillation column at a rate such that the weight ratio of the glycerol feed stream to the reaction product stream introduced into the extractive distillation column is at least 1:10. In other embodiments, the glycerol feed stream may be introduced into the extraction distillation column at a rate such that the weight ratio of the glycerol feed stream to the reaction product stream introduced into the extractive distillation column is at least 1:4.

In certain embodiments, the glycerol feed stream may be introduced into the extraction distillation column at a rate such that the weight ratio of the glycerol feed stream to the reaction product stream introduced into the extractive distillation column is at most 10:1. In certain embodiments, the glycerol feed stream may be introduced into the extraction distillation column at a rate such that the weight ratio of the glycerol feed stream to the reaction product stream introduced into the extractive distillation column is at most 5:1. In other embodiments, the glycerol feed stream may be introduced into the extraction distillation column at a rate such that the weight ratio of the glycerol feed stream to the reaction product stream introduced into the extractive distillation column is at most 1.5:1.

In certain embodiments, the water feed stream may be pure water or may comprise one or more contaminants. In certain embodiments, the water feed stream may comprise liquid water. In other embodiments, the water feed stream may comprise water vapor or steam.

In certain embodiments, the water feed stream may be introduced into the extractive distillation column at a rate such that the weight ratio of the water feed stream to the reaction product stream and glycerol feed stream introduced into the extraction distillation column may be a ratio in the range of from 1:10,000 to 1:10. In certain embodiments, the water feed stream may be introduced into the extractive distillation column at a rate such that the weight ratio of the water feed stream to the reaction product stream and glycerol feed stream introduced into the extraction distillation column may be a ratio in the range of from 1:1000 to 1:20. In certain embodiments, the water feed stream may be introduced into the extractive distillation column at a rate such that the weight ratio of the water feed stream to the reaction product stream and glycerol feed stream introduced into the extraction distillation column may be a ratio in the range of from 1:500 to 1:50. In certain embodiments, the water feed stream may be introduced into the extractive distillation column at a rate such that the weight ratio of the water feed stream to the reaction product stream and glycerol feed stream introduced into the extraction distillation column may be a ratio in the range of from 1:100 to 1:10. In certain embodiments, the water feed stream may be introduced into the extractive distillation column at a rate such that the weight ratio of the water feed stream to the reaction product stream and glycerol feed stream introduced into the extraction distillation column may be a ratio in the range of from 1:10,000 to 1:100.

In certain embodiments, the water feed stream may be provided to the bottom of the extractive distillation column by providing the water feed stream to a reboiler. In certain embodiments, the water feed stream may be provided to the bottom of the extractive distillation column by combining the water feed stream with the reaction product stream and/or the glycerol feed stream. In certain embodiments, the water feed stream may be directly provided to the bottom of the extractive distillation column.

In certain embodiments, operating the extractive distillation column may comprise operating the extractive distillation column at a temperature in the range of from 50° C. to 250° C. and a pressure in the range of from 0.1 kPa to 400 kPa. In certain embodiments, operating the extractive distillation column may comprise operating the extractive distillation column at a temperature in the range of from 120° C. to 230° C. and a pressure in the range of from 0.1 kPa to 200 kPa.

In certain embodiments, operating the extractive distillation column may comprise allowing the water from the water feed stream to vaporize in the extractive distillation column. In certain embodiments, operating the extractive distillation column may comprise allowing any vaporized water in the extractive distillation column to generate a water partial pressure in a vapor flow in the extractive distillation column. In certain embodiments, operating the extractive distillation column may comprise allowing any water vapor provided to the extractive distillation column to generate a water partial pressure in a vapor flow in the extractive distillation column. In certain embodiments, operating the extractive distillation column comprises allowing the water partial pressure to provide a thermodynamic driving force to avoid and/or limit thermal condensation and elimination reactions in the extractive distillation column.

In certain embodiments, operating the extractive distillation column may comprise generating a tops recovery stream and a bottoms recovery stream. In certain embodiments, a portion of the tops recovery stream may be recycled to the top of the extractive distillation column. In certain embodiments, a portion of the bottoms recovery stream may be recycled to the bottom of the extractive distillation column.

In certain embodiments, the tops recovery stream may comprise a mixture tops stream. In certain embodiments, the tops recovery stream may be split into the mixture tops stream and a water vapor stream with a partial condenser at the top of the extractive distillation column.

In certain embodiments, the tops recovery stream may comprise MPG, 1,2-BDO, 1,2-PDO, and water with a water concentration depending on the configurations and conditions of the top section of the extractive distillation column. In cases where a partial condenser is used, the condensation temperature at given pressure level results in an equilibrium water content in the mixture tops stream and an equilibrium MPG, 1,2-BDO, and 1,2-PDO content in the water vapor stream. In certain embodiments, the partial condenser may be replaced with a rectification section in the top of the extractive distillation column. In such embodiments, the mixture tops stream may be drawn as a side stream from the upper part of the extractive distillation column and the water vapor stream may be drawn as tops stream from the extractive distillation column.

In certain embodiments, the bottoms recovery stream may comprise the mixture feed stream. In certain embodiments, the mixture feed stream may comprise MEG and glycerol.

In certain embodiments, the amount of MEG in the mixture feed stream may be an amount in the range of from 10 wt. % to 90 wt. % based on the overall weight of the mixture feed stream. In certain embodiments, the amount of MEG in the mixture feed stream may be an amount in the range of from 20 wt. % to 80 wt. % based on the overall weight of the mixture feed stream. In certain embodiments, the amount of MEG in the mixture feed stream may be an amount in the range of from 30 wt. % to 60 wt. % based on the overall weight of the mixture feed stream.

In certain embodiments, the amount of glycerol in the mixture feed stream may be an amount in the range of from 10 wt. % to 90 wt. % based on the overall weight of the mixture feed stream. In certain embodiments, the amount of glycerol in the mixture feed stream may be an amount in the range of from 20 wt. % to 80 wt. % based on the overall weight of the mixture feed stream. In certain embodiments, the amount of glycerol in the mixture feed stream may be an amount in the range of from 40 wt. % to 70 wt. % based on the overall weight of the mixture feed stream.

In certain embodiments, the mixture feed stream may further comprise one or more contaminants originating from upstream processes.

In certain embodiments, as discussed above, the mixture feed stream may be introduced into a solvent recovery column.

In certain embodiments, the water feed stream may be recycled from the water vapor stream.

In certain embodiments, the present disclosure describes a method comprising: providing a reaction product stream to an extractive distillation column; providing a glycerol feed stream to the extractive distillation column above the reaction product stream; providing a first water feed stream to the bottom of the extractive distillation column; operating the extractive distillation column; removing a mixture feed stream comprising MEG and glycerol from the extractive distillation column; providing the mixture feed stream to a solvent recovery column; providing a second water feed stream to the bottom of the solvent recovery; operating the solvent recovery column; and removing an MEG recovery stream from the solvent recovery column.

In certain embodiments, the reaction product stream may comprise any reaction product stream discussed above. In certain embodiments, the glycerol feed stream may comprise any glycerol feed stream discussed above. In certain embodiments, first water feed stream may comprise any water feed stream discussed above. In certain embodiments, the mixture feed stream may comprise any mixture feed stream discussed above. In certain embodiments, the second water feed stream may comprise any water feed stream discussed above. In certain embodiments, the MEG recovery stream may comprise any MEG recovery stream discussed above.

In certain embodiments, the extractive distillation column may comprise any extractive distillation column discussed above. In certain embodiments, operating the extractive distillation column may comprise operating the extractive distillation column in any manner discussed above. In certain embodiments, operating the extractive distillation column may comprise generating a tops recovery stream and a bottoms recovery stream. In certain embodiments, the tops recovery stream may comprise any tops recovery stream discussed above. In certain embodiments, the bottoms recovery stream may comprise any bottoms recovery stream discussed above.

In certain embodiments, the solvent recovery column may comprise any solvent recovery column discussed above. In certain embodiments, operating the solvent recovery column may comprise operating the solvent recovery column in any manner discussed above. In certain embodiments, operating the solvent recovery column may comprise generating a tops recovery stream and a bottoms recovery stream. In certain embodiments, the tops recovery stream may comprise any tops recovery stream discussed above. In certain embodiments, the bottoms recovery stream may comprise any bottoms recovery stream discussed above.

Referring now to FIG. 1, FIG. 1 illustrates a non-limiting embodiment of the present disclosure.

In certain embodiments, stream 101, stream 102, and stream 103 may be provided to distillation column 104. In certain embodiments, stream 101 may comprise any reaction product stream discussed above. In certain embodiments, stream 102 may comprise any glycerol feed stream discussed above. In certain embodiments, stream 103 may comprise any water feed stream or first water feed stream discussed above. In certain embodiments, distillation column 104 may comprise any extractive distillation column discussed above. In certain embodiments, stream 105 and stream 106 may be recovered from distillation column 104. In certain embodiments, stream 105 may comprise any bottoms recovery stream discussed above. In certain embodiments, stream 105 may comprise any mixture feed stream discussed above. In certain embodiments, stream 106 may comprise any tops recovery stream discussed above. In certain embodiments, not illustrated in FIG. 1, stream 106 may comprise a first tops stream and a second tops stream. In such embodiments, the first tops stream may comprise any mixture tops stream discussed above and the second tops stream may comprise any water vapor stream discussed above.

In certain embodiments, stream 105 and stream 107 may be provided to distillation column 108. In certain embodiments, stream 107 may comprise any water feed stream or second water feed stream discussed above. In certain embodiments, distillation column 108 may comprise any solvent recovery column discussed above.

In certain embodiments, stream 109 and stream 110 may be recovered from distillation column 108. In certain embodiments, stream 109 may comprise any bottoms recovery stream discussed above. In certain embodiments, stream 109 may comprise any glycerol feed stream discussed above. In certain embodiments, a portion or all of stream 109 may recycled to stream 102. In certain embodiments, stream 110 may comprise any tops recovery stream discussed above. In certain embodiments, not illustrated in FIG. 1, stream 110 may comprise a first tops stream and a second tops stream. In such embodiments, the first tops stream may comprise any MEG recovery stream discussed above and the second tops stream may comprise any water vapor stream discussed above.

EXAMPLES

The invention will be further illustrated by the following, non-limiting examples.

The performance of a glycol separation process in accordance to the process illustrated in FIG. 1 was evaluated. A glycol feed stream with varying amounts of MEG (45 wt. % to 80 wt. %), MPG (10 wt. % to 25 wt. %), 1,2-BDO (10 wt. % to 25 wt. %), 1,2-PDO (0 wt. % to 5 wt. %), and 1,2-HDO (0 wt. % to 5 wt. %) was fed into an extractive distillation column at a varied rate (50 g/hr to 60 g/hr). Varying amounts of a water feed stream (0 g/hr to 5.5 g/hr) and a glycerol feed stream (100 g/hr to 200 g/hr) were also fed into the extractive distillation column. The extractive distillation column was operated with a bottom pressure varying from 20 mbar to 150 mbar and a bottom temperature varying from 80° C. to 190° C. A bottoms recovery stream was recovered from the extractive distillation column and fed into a solvent recovery column along with varying amounts of a water feed stream (0 g/hr to 5.5 g/hr). The solvent recovery column was operated with a bottom pressure varying from 10 mbar to 50 mbar and a bottom temperature varying from 100° C. to 210° C. In some instances, air leaked into the column leading to oxidation reactions.

An MEG recovery stream was recovered from the solvent recovery column. The off-specification frequency of the MEG recovery stream was evaluated using UV specification performance Table 1 below shows the off-specification frequency averages for varying UV wavelengths when no water feed streams were introduced into the columns compare to when water feed streams were introduced into the columns. All off-specification cases with water dosing were related to the above-mentioned air leakages.

TABLE 1

| Wavelength | Without Water | With Water |
|---|---|---|
| 350 nm | 70% | 0% |
| 275 nm | 79% | 5% |
| 250 nm | 58% | 3% |
| 220 nm | 49% | 3% |

It was found that when water was introduced into the columns, the MEG product analyses showed a better than fiber grade quality and when no water was introduced into the columns, the MEG product analyses showed a lower than fiber grade quality.

That which is claimed is:

1. A method for separating oxygenates, the method comprising:
providing a stream comprising oxygenates to a distillation column;
providing a water feed stream to a bottom of the distillation column;
operating the distillation column at higher temperatures than the thermal stability of the oxygenates;
removing a first recovery stream comprising a first portion of the oxygenates from the distillation column at a point above the oxygenates; and
removing a second recovery stream comprising a second portion of the oxygenates from the distillation column at a point below the oxygenates.

2. The method of claim 1, wherein operating the distillation column comprises vaporizing a portion of the water to generate a water partial pressure in a vapor flow in the distillation column, wherein the water partial pressure provides a thermodynamic driving force to avoid and/or limit thermal condensation and elimination reactions in the distillation column.

3. The method of claim 1, wherein a weight ratio of the amount of water feed stream provided to the distillation column to the amount of stream provided to the distillation column is a ratio in the range of from 1:10,000 to 1:100.

4. The method of claim 1, wherein the stream comprises at least one of monoethylene glycol (MEG), monopropylene glycol (MPG) or mixtures thereof.

5. The method of claim 1, wherein the stream further comprises glycerol.

6. The method of claim 4, wherein operating the distillation column comprises operating at a temperature from 150° C. to 250° C. and pressure of 0.1 to 100 kPa.

7. The method of claim 4, wherein the first recovery stream further comprises water and the process further comprises separating the MEG and water and recycling the water to the distillation column.

8. The method of claim 1, wherein the oxygenates comprise MEG and 1,2-butanediol (1,2-BDO).

9. The method of claim 1, wherein the oxygenates comprise MPG and 1,2-pentanediol (1,2-PDO).

10. The method of claim 8, wherein the oxygenates are generated from the hydrogenolysis of a saccharide containing feedstock.

11. The method of claim 1, wherein the distillation column is an extractive distillation column and the process further comprises:
providing a solvent feed stream comprising solvent to the extractive distillation column above the oxygenates;
operating the extractive distillation column to vaporize at least a portion of the water feed stream;
removing the first recovery stream from the extractive distillation column above the solvent feed stream; and
removing the second recovery stream with the solvent below the solvent feed stream.

12. The method of claim 11, wherein the solvent feed stream comprises glycerol.

13. The method of claim 12, wherein the first portion of the oxygenates comprises 1,2-butanediol and the second portion of the oxygenates comprises MEG.

14. The method of claim 12, wherein the first portion of the oxygenates comprises 1,2-pentanediol and the second portion of the oxygenates comprises MPG.

15. The method of claim 12, wherein the oxygenates are generated from the hydrogenolysis of a saccharide containing feedstock.

16. The method of claim 12, wherein operating the extractive distillation column comprises vaporizing at least a portion of the water feed stream to generate a water partial pressure in a vapor flow in the extractive distillation column to provide a thermodynamic driving force to avoid and/or limit thermal condensation and elimination reactions in the extractive distillation column.

17. The method of claim 11, wherein a weight ratio of the amount of water feed stream provided to the extractive distillation column to the amount of the stream and the solvent stream provided to the extractive distillation column is a ratio in the range of from 1:10,000 to 1:100.

18. The method of claim 11, wherein operating the extractive distillation column comprises operating at a temperature from 150° C. to 250° C. and pressure of 0.1 to 100 kPa.

* * * * *